(12) United States Patent
Tanaka

(10) Patent No.: US 9,186,040 B2
(45) Date of Patent: Nov. 17, 2015

(54) SEALING STRUCTURE AND ANTENNA APPARATUS

(71) Applicant: OLYMPUS MEDICAL SYSTEMS CORP., Tokyo (JP)

(72) Inventor: Shinsuke Tanaka, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 246 days.

(21) Appl. No.: 13/975,906

(22) Filed: Aug. 26, 2013

(65) Prior Publication Data

US 2014/0058196 A1    Feb. 27, 2014

Related U.S. Application Data

(63) Continuation of application No. PCT/JP2012/080478, filed on Nov. 26, 2012.

(30) Foreign Application Priority Data

Mar. 30, 2012  (JP) .................................. 2012-082517

(51) Int. Cl.
*A61B 1/00* (2006.01)
*H01Q 7/02* (2006.01)
*H05K 5/03* (2006.01)
(Continued)

(52) U.S. Cl.
CPC ........ *A61B 1/00016* (2013.01); *H01L 23/3121* (2013.01); *H01L 23/3135* (2013.01); *H05K 5/0047* (2013.01); *A61B 1/041* (2013.01); *H01L 2924/0002* (2013.01); *H05K 1/189* (2013.01)

(58) Field of Classification Search
CPC ............. A61B 1/00016; A61B 1/0011; A61B 1/00114; A61B 1/041; H01L 23/3121; H01L 23/3135; H05K 5/0047; H05K 5/0052; H05K 5/0095; H05K 1/189; H01Q 7/02
USPC .......................................................... 343/872
See application file for complete search history.

(56) References Cited

U.S. PATENT DOCUMENTS 4,597,617 A     7/1986 Enochs
5,208,728 A *   5/1993 Schirmer ...................... 361/752
(Continued)

FOREIGN PATENT DOCUMENTS

JP      54-54267        4/1979
JP      60-211964 A     10/1985
(Continued)

OTHER PUBLICATIONS

Decision of a Patent Grant dated Sep. 17, 2013 from related Japanese Patent Application No. 2013-536741, together with an English language translation.
(Continued)

*Primary Examiner* — John P Leubecker
(74) *Attorney, Agent, or Firm* — Scully, Scott, Murphy & Presser, PC

(57) ABSTRACT

A sealing structure has: a plate portion that is formed with a harder material than a bendable substrate and interposes an electronic device via the substrate from a top surface and a back surface of the substrate on which the electronic device is mounted; and an elastic body that is provided on an outer periphery of the plate portion to cover a part of the plate portion and integrally molded so as to press the plate portion against the substrate.

9 Claims, 13 Drawing Sheets

(51) Int. Cl.
*H05K 5/00* (2006.01)
*H01L 23/31* (2006.01)
*H05K 1/18* (2006.01)
*A61B 1/04* (2006.01)

(56) References Cited

U.S. PATENT DOCUMENTS

| | | | | |
|---|---|---|---|---|
| 5,392,197 | A * | 2/1995 | Cuntz et al. | 361/818 |
| 6,426,461 | B1 * | 7/2002 | Ginter et al. | 174/540 |
| 7,768,465 | B2 * | 8/2010 | Jared et al. | 343/713 |
| 2007/0120755 | A1 * | 5/2007 | Blickle | 343/713 |
| 2008/0053700 | A1 * | 3/2008 | O'Connor et al. | 174/564 |
| 2008/0055184 | A1 * | 3/2008 | Noro et al. | 343/872 |
| 2011/0170269 | A1 * | 7/2011 | Blossfeld et al. | 361/752 |
| 2014/0085823 | A1 * | 3/2014 | Campbell et al. | 361/701 |

FOREIGN PATENT DOCUMENTS

| | | |
|---|---|---|
| JP | 6-318419 A | 11/1994 |
| JP | 6-326151 A | 11/1994 |
| JP | 2003-179326 A | 6/2003 |
| JP | 2007-330508 A | 12/2007 |
| JP | 2011-248582 A | 12/2011 |

OTHER PUBLICATIONS

International Search Report dated Feb. 26, 2013 from related International Application No. PCT/JP2012/080478.

* cited by examiner

SEALING STRUCTURE AND ANTENNA APPARATUS

CROSS REFERENCES TO RELATED APPLICATIONS

This application is a continuation of PCT International Application No. PCT/JP2012/080478 filed on Nov. 26, 2012, designating the United States, incorporated herein by reference, and claiming the benefit of priority from Japanese Patent Application No. 2012-082517, filed on Mar. 30, 2012 and also incorporated herein by reference.

BACKGROUND OF THE INVENTION

1. Field of the Invention

The present invention relates to: a sealing structure that seals an electronic device mounted on a substrate of an antenna apparatus that receives a wireless signal transmitted from a capsule endoscope inserted into a subject; and the antenna apparatus.

2. Description of the Related Art

Hitherto, in the field of endoscopes, a capsule endoscope, which has an imaging function, a radio communication function, and the like accommodated in a capsule-shaped housing formed in a size capable of being introduced into the digestive tract of a subject such as a patient, has been known. After being swallowed from the mouth of the subject, the capsule endoscope generates image data by sequentially capturing images of inside of the subject, while moving inside the subject, such as in the digestive tract, by the peristaltic movement or the like, and sequentially transmits the image data wirelessly.

The image data wirelessly thus transmitted by the capsule endoscope is received by a receiving device via a receiving antenna apparatus provided outside the subject. The receiving device has a memory that stores therein the received image data, and is portable by the subject.

As the antenna apparatus described above, an apparatus in which a plurality of receiving antennas are distributively arranged on a flexible sheet has been known. In the antenna apparatus, one receiving antenna having the greatest receiving strength of the wireless signal is selected, and the wireless signal is received by the selected receiving antenna (see Japanese Laid-open Patent Publication No. 2007-330508).

SUMMARY OF THE INVENTION

A sealing structure according to an aspect of the present invention is a sealing structure that seals an electronic device mounted on a substrate that is bendable, the sealing structure including: a plate portion that is formed with a harder material than the substrate and interposes the electronic device via the substrate from a top surface and a back surface of the substrate on which the electronic device is mounted; and an elastic body that is provided on an outer periphery of the plate portion to cover a part of the plate portion and integrally molded so as to press the plate portion against the substrate.

An antenna apparatus according to another aspect of the present invention is an antenna apparatus that receives a wireless signal transmitted from a capsule endoscope introduced into a subject, the antenna apparatus including: a substrate that is bendable; an antenna unit that is mounted on the substrate and receives the wireless signal; an electronic device that is mounted on the substrate and connected to the antenna unit to perform a predetermined process on the wireless signal received by the antenna unit; and a sealing structure that seals the electronic device, and this sealing structure has: a plate portion that is formed with a harder material than the substrate and interposes the electronic device via the substrate from a top surface and a back surface of the substrate on which the electronic device is mounted; and an elastic body that is provided on an outer periphery of the plate portion to cover a part of the plate portion and integrally molded so as to press the plate portion against the substrate.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
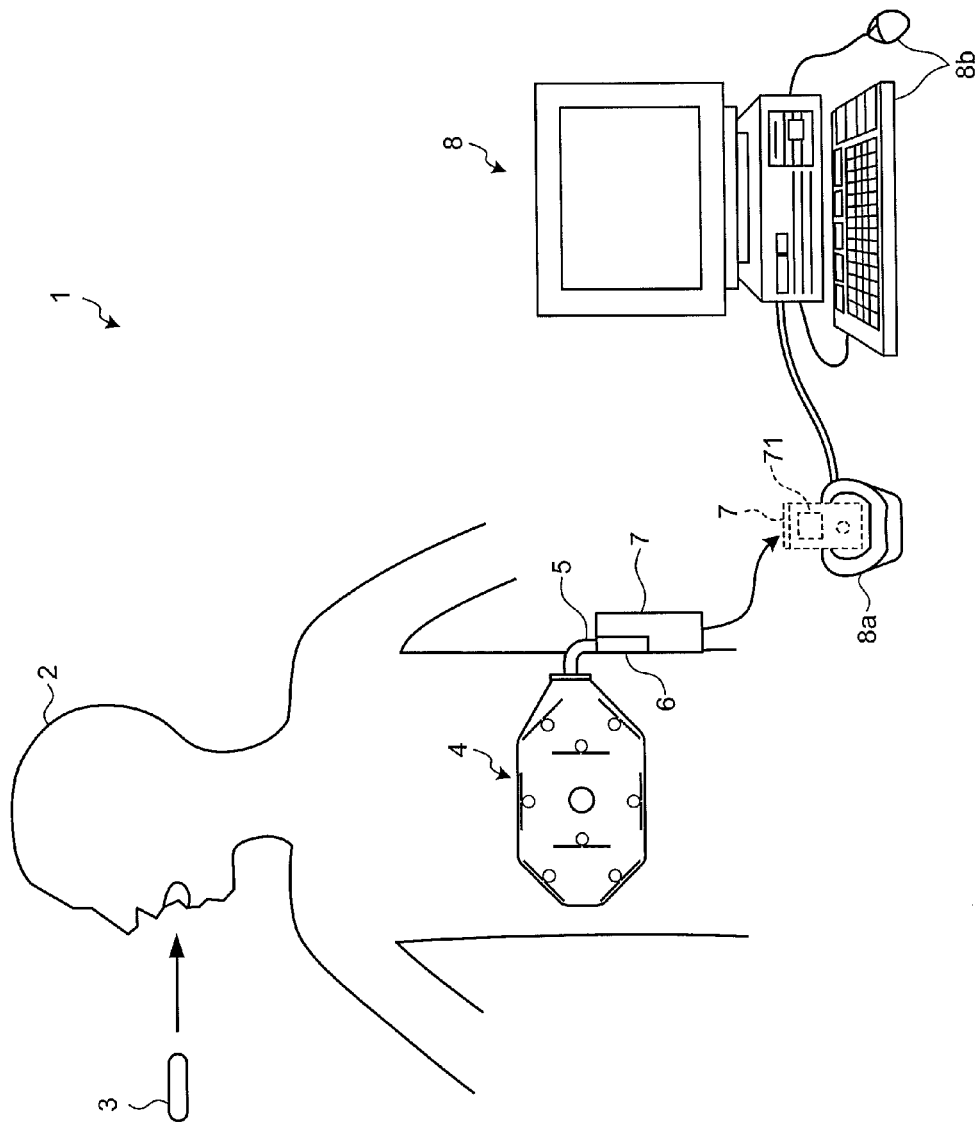
FIG. 1 is a schematic diagram illustrating a schematic configuration of a capsule endoscope system according to a first embodiment of the invention.

Hereinafter, sealing structures configured to seal electronic devices mounted on substrates according to embodiments of the invention will be described with reference to the drawings. In addition, in the following description, as an example of a sealing structure according to the invention, an example of a capsule endoscope system including an antenna apparatus configured to receive a wireless signal from a capsule endoscope introduced into a body of a subject to capture an in-vivo image of the subject will be described, but the invention is not intended to be limited by the embodiments. Furthermore, in the following description, the same structures will be denoted by the same reference numerals.

First Embodiment

FIG. 1 is a schematic diagram illustrating a schematic configuration of a capsule endoscope system according to a first embodiment of the invention.

As illustrated in FIG. 1, a capsule endoscope system 1 includes a capsule endoscope 3 that captures in-vivo images of a subject 2, an antenna apparatus 4 that receives wireless signals transmitted from the capsule endoscope 3 introduced into the subject 2, an antenna connection unit 6 that performs a predetermined process on the wireless signals input from the antenna apparatus 4 via an antenna cable 5, a receiving device 7 that performs a predetermined process on a signal input from the antenna connection unit 6 to perform recording, and an image processing apparatus 8 that processes and/or displays an image corresponding to image data within the subject 2 captured by the capsule endoscope 3. In addition, the antenna apparatus 4 is mounted to the subject 2 by being inserted into an antenna holder which is not illustrated. In addition, the receiving device 7 is mounted to the subject 2 by being inserted into a receiving device holder which is not illustrated.

The capsule endoscope 3 has an imaging function of capturing images inside the subject 2, and a wireless communication function of transmitting image data obtained by capturing the images inside the subject 2 to the antenna apparatus 4. Furthermore, an antenna with a circular coil or a circular loop is arranged within the capsule endoscope 3. The capsule endoscope 3 passes through the esophagus of the subject 2 by being swallowed into the subject 2, and moves inside the body cavity by the peristaltic movement of the gastrointestinal tract lumen. The capsule endoscope 3 sequentially captures the images inside the body cavity of the subject 2 at a small time interval, for example, at an interval of 0.5 second, while moving inside the body cavity, and generates the captured image data in the subject 2 to sequentially transmit the image data to the antenna apparatus 4. In this case, the capsule endoscope 3 generates a transmission signal that includes the image data, and a received strength detection data including the position information (beacon) making it easier to detect the received strength or the like, and wirelessly transmits a wireless signal obtained by modulating the generated transmission signal to the antenna apparatus 4.

The antenna apparatus 4 periodically receives the wireless signal from the capsule endoscope 3, and outputs the wireless signal to the antenna connection unit 6 via the antenna cable 5.

The antenna cable 5 is formed by using a coaxial cable. The antenna cable 5 propagates the wireless signal received by the antenna apparatus 4 to the antenna connection unit 6.

The antenna connection unit 6 is freely attachable to and detachable from the receiving device 7. The antenna connection unit 6 performs extraction of the image data in the subject 2, and the detection of the received strength depending on the strength of the wireless signal, based on the wireless signal transmitted from the capsule endoscope 3 via the antenna apparatus 4 and the antenna cable 5.

The receiving device 7 acquires the image data in the subject 2 based on the wireless signal transmitted from the capsule endoscope 3 via the antenna connection unit 6. The receiving device 7 stores position information and time information indicating time or the like in a memory correspondingly with the received image data. While the capturing is performed by the capsule endoscope 3, for example, until the receiving device 7 is introduced from the mouth of the subject 2, passes through the interior of the gastrointestinal tract, and is excreted from the interior of the subject 2, the receiving device 7 is housed in the receiving device holder, and is carried by the subject 2. After completion of the examination using the capsule endoscope 3, the receiving device 7 is detached from the subject 2, and is connected to the image processing apparatus 8 for transmission of information such as image data received from the capsule endoscope 3. In addition, when the antenna connection unit 6 detects disconnection of the antenna cable 5, the receiving device 7 performs display indicating the disconnection of the antenna on a display unit 71 of the receiving device 7. In addition, the display unit 71 of the receiving device 7 has a viewer function allowing viewing of the acquired images, and to prevent overuse of this viewer function, means are provided, for notifying a user if a residual quantity of a battery of a power supply unit inside the receiving device 7 becomes a capacity that is unable to guarantee an assumed inspection time.

The image processing apparatus 8 is constituted by using a workstation including a display unit such as a liquid crystal display or a personal computer. The image processing apparatus 8 displays an image corresponding to the image data in the subject 2 acquired via the receiving device 7.

Furthermore, the image processing apparatus 8 includes a cradle 8a configured to read the image data from the memory of the receiving device 7, and an operation input device 8b such as a keyboard and a mouse. The cradle 8a acquires the image data, and the related information such as the received strength information associated with the image data, the time information and the identification information of the capsule endoscope 3 from the memory of the receiving device 7 when the receiving device 7 is mounted, and the cradle 8a transmits the various acquired information to the image processing apparatus 8. The operation input device 8b receives the input from the user.

Accordingly, a user observes the biological sites inside the subject 2, for example, the esophagus, the stomach, the small intestine, the large intestine, or the like, and diagnoses the subject 2, while operating the operation input device 8b, and looking at the images in the subject 2 sequentially displayed by the image processing apparatus 8. Furthermore, the image processing apparatus 8 is adapted to acquire the antenna identification information that is output from the antenna connection unit 6 via the receiving device 7, and to change the process of position detection per type of antenna. Furthermore, the image processing apparatus 8 is configured to determine abnormality based on antenna failure information that is output from the receiving device 7, and to switch over the position detection information display. The cradle 8a is provided with a falling-out preventing binder so as to prevent the cable connecting the image processing apparatus 8 from falling out.

Figure 2:
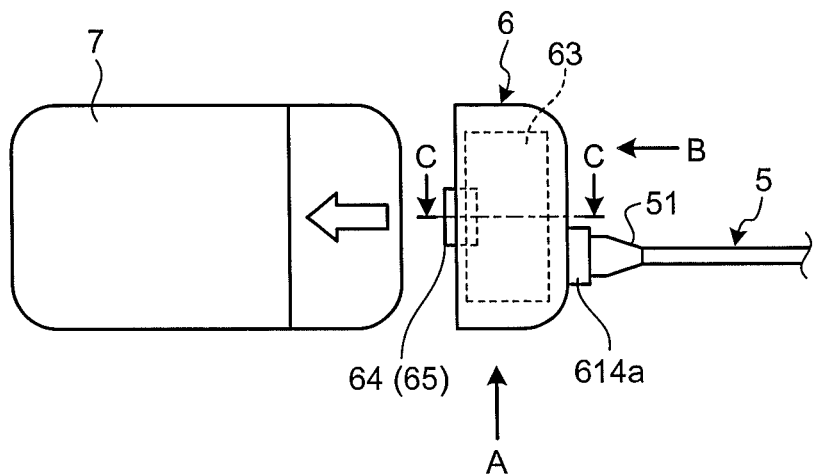
FIG. 2 is a top view of a state in which an antenna connection unit and a receiving device according to the first embodiment of the invention are separated from each other.
Figure 3:
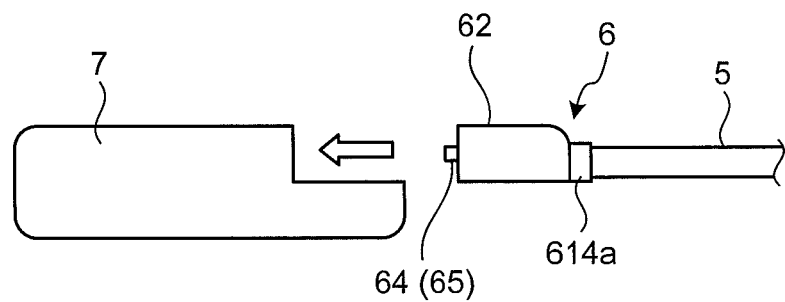
FIG. 3 is a side view seen from a direction of an arrow A of FIG. 2.
Figure 4:
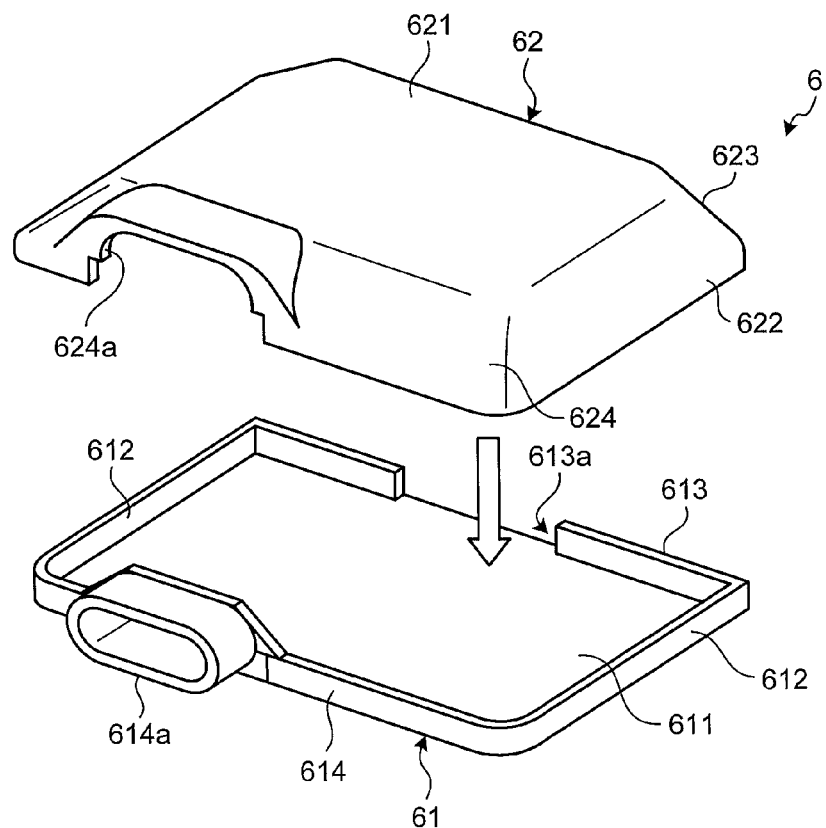
FIG. 4 is an exploded perspective view of a housing of the antenna connection unit according to the first embodiment of the invention.
Figure 5:
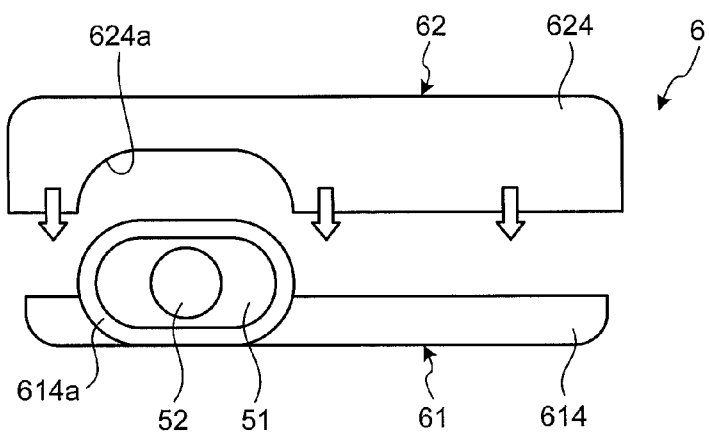
FIG. 5 is an exploded front view of the housing of the antenna connection unit taken along a direction of an arrow B of FIG. 2.
Figure 6:
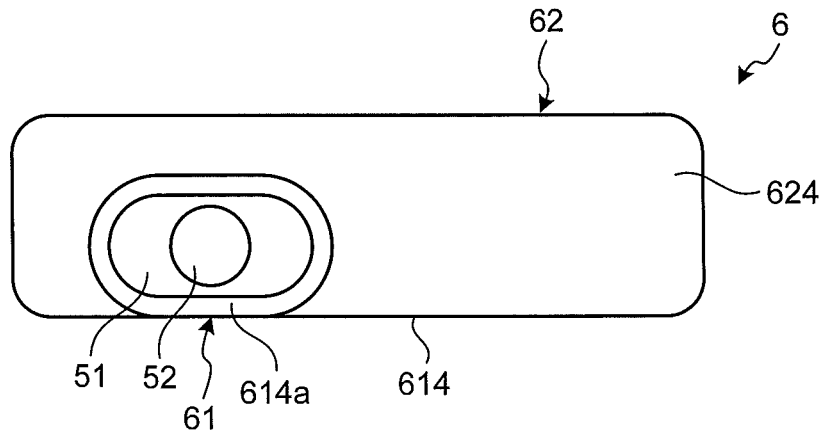
FIG. 6 is a front view of the antenna connection unit taken along the direction of the arrow B of FIG. 2.

Next, a configuration of a general overview of the structure of the antenna connection unit 6 illustrated in FIG. 1 will be described in detail. FIG. 2 is a top view of a state in which the antenna connection unit 6 and the receiving device 7 are separated from each other. FIG. 3 is a side view from a direction of an arrow A of FIG. 2. FIG. 4 is an exploded perspective view of a housing of the antenna connection unit 6. FIG. 5 is an exploded front view of the housing of the antenna connection unit 6 taken along a direction of an arrow B of FIG. 2. FIG. 6 is a front view of the antenna connection unit 6 taken along the direction of the arrow B of FIG. 2.

As illustrated in FIGS. 2 to 6, the antenna connection unit 6 includes a lower housing 61 having an approximately rectangular shape formed so as to cover the bottom surface, an upper housing 62 having an approximately rectangular shape formed so as to cover the top surface and the side surface, a processing substrate 63 which performs predetermined processing, and a connector unit 64 connected to the receiving device 7. By coupling the lower housing 61 and the upper housing 62 in a state of being opposed to each other, the antenna connection unit 6 is formed in a box shape of an approximately rectangle having a space therein, and the connector unit 64 and the processing substrate 63 are accommodated therein.

The lower housing 61 has a bottom portion 611 having an approximately rectangular shape, is provided with side portions 612 facing each other on the periphery of the bottom portion 611, a rear portion 613, and a front portion 614 in an upright state, and is formed with an upper side thereof opened. The front portion 614 has a holding portion 614a which holds a bend stopper portion 51 of the antenna cable 5. The holding portion 614a has an approximately tubular shape, and is formed to have a thickness on the side wall. Furthermore, the rear portion 613 has a notch portion 613a that holds the connector unit 64 via a gasket portion 65. The bottom portion 611, the side portions 612, the rear portion 613, the front portion 614, and the holding portion 614a are integrally formed by injection molding so as to continuously extend, using a plastic material such as plastic. Thus, it is possible to increase the rigidity against an external force applied to the bend stopper portion 51 of the antenna cable 5, and it is possible to prevent the antenna connection unit 6 from being opened by the external force.

The upper housing 62 has an upper portion 621 that forms a rectangular shape, is provided with side portions 622 facing each other on the periphery of the upper portion 621, a rear portion 623, and a front portion 624 in a state of extending downward, and is formed with a lower side thereof opened. The front portion 624 has a notch portion 624a which is formed to match the shape of the holding portion 614a. Furthermore, the rear portion 623 has a notch portion 623a that holds the connector unit 64 via the gasket portion 65. The upper portion 621, the side portions 622, the rear portion 623, and the front portion 624 are integrally formed by injection molding so as to continuously extend, using a plastic material. Accordingly, since the notch portion 624a is pressed against the holding portion 614a of the lower housing 61, it is possible to further increase the rigidity against the external force applied to the bend stopper portion 51 of the antenna cable 5, and it is possible to prevent the antenna connection unit 6 from being opened by the external force.

Figure 7:
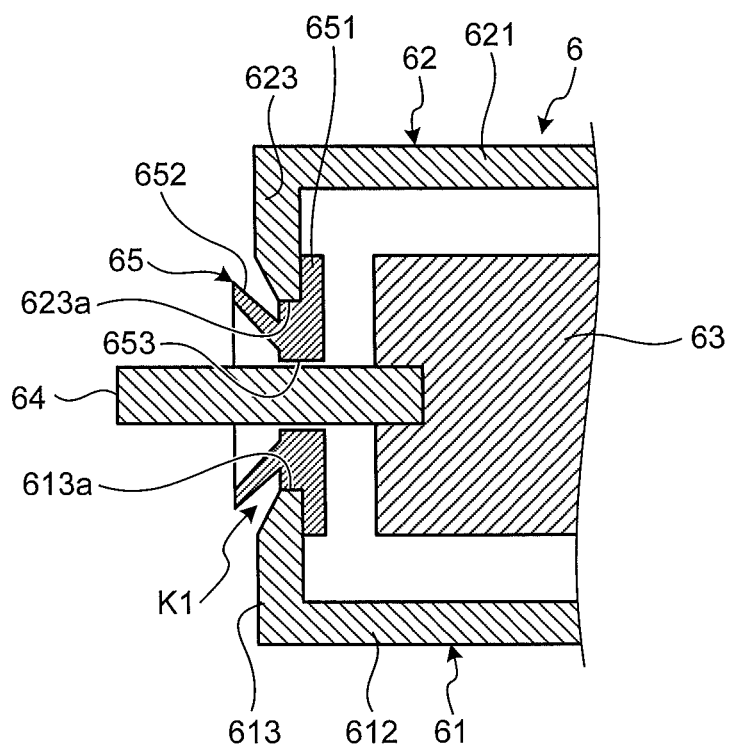
FIG. 7 is a diagram schematically illustrating a main part of a cross section taken along line C-C of FIG. 2.

Here, the structure of the gasket portion 65 will be described in detail. FIG. 7 is a diagram schematically illustrating the main part of the cross section taken along line C-C of FIG. 2.

Figure 8:
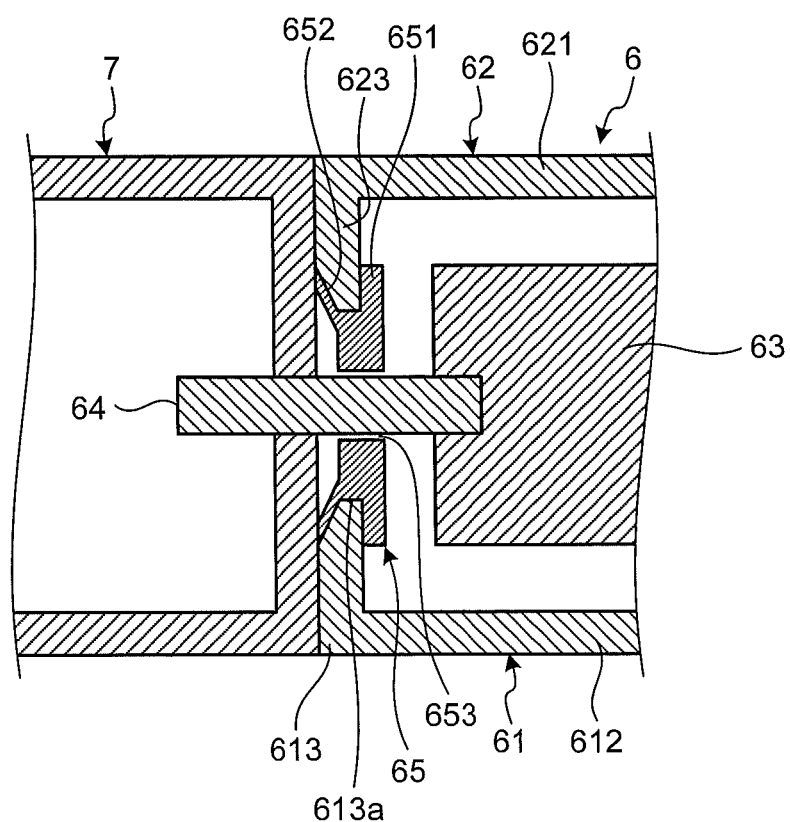
FIG. 8 is a cross-sectional view schematically illustrating a state of a gasket when the antenna connection unit according to the first embodiment of the invention is connected to the receiving device.

As illustrated in FIG. 7, the gasket portion 65 is configured using an elastic member such as a silicone rubber. The gasket portion 65 has a bottom portion 651 having an approximately rectangular shape, and is formed with a distal end portion 652 that extends from the outer surface of the bottom portion 651 at an acute angle and has an approximately conical shape (a tapered shape). The gasket portion 65 includes a connector holding portion 653 having an approximately rectangular shape that holds the connector unit 64 at the center thereof. The gasket portion 65 is accommodated in the antenna connection unit 6 by being interposed between the notch portion 613a of the rear portion 613 of the lower housing 61 and the notch portion 623a of the rear portion 623 of the upper housing 62 in a state in which the distal end portion 652 is exposed from the antenna connection unit 6. Accordingly, when the antenna connection unit 6 is connected to the receiving device 7, the distal end portion 652 is pressed against the wall surface of the receiving device 7, and thus, the gasket portion 65 is able to infallibly provide watertightness between the antenna connection unit 6 and the receiving device 7. Furthermore, when the antenna connection unit 6 is connected to the receiving device 7, and the distal end portion 652 is pressed against the wall surface of the receiving device 7, since the distal end portion 652 spreads in a space K1 (see FIG. 8), the gasket portion 65 is able to infallibly provide watertightness between the antenna connection unit 6 and the receiving device 7 without the volume of the distal end portion 652 being compressed.

Figure 9:
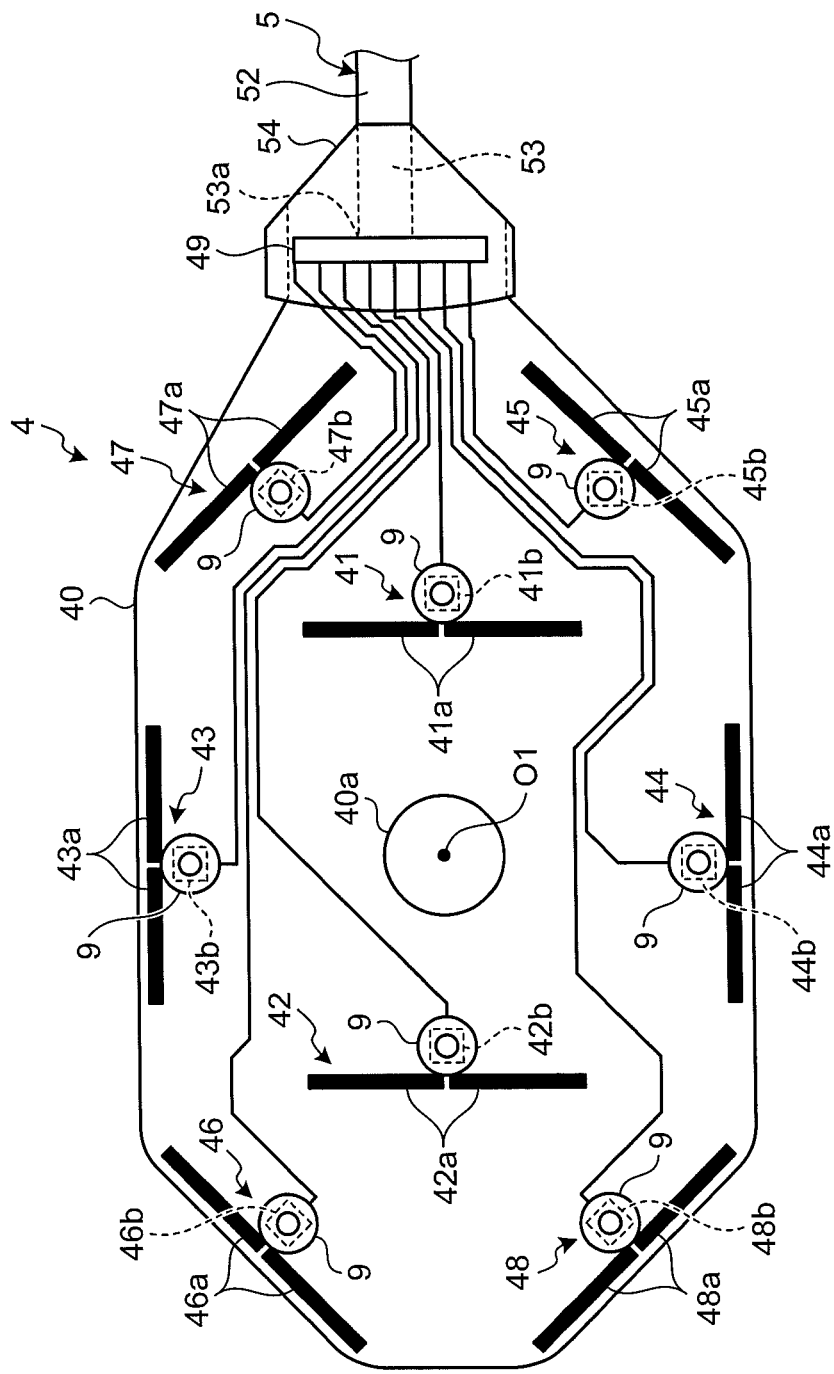
FIG. 9 is a schematic diagram illustrating a configuration of the antenna apparatus and an antenna cable according to the first embodiment of the invention.

Next, the detailed configuration of the antenna apparatus 4 and the antenna cable 5 illustrated in FIG. 1 will be described. FIG. 9 is a schematic view illustrating a structure of the antenna apparatus 4 and the antenna cable 5.

As illustrated in FIG. 9, the antenna apparatus 4 includes a polygonal sheet 40, a first receiving antenna 41, a second receiving antenna 42, a third receiving antenna 43, a fourth receiving antenna 44, a fifth receiving antenna 45, a sixth receiving antenna 46, a seventh receiving antenna 47, an eighth receiving antenna 48, and a connector unit 49. The first receiving antenna 41 to the eighth receiving antenna 48 are each connected to the connector unit 49, and are provided on one polygonal sheet 40. In addition, in FIG. 9, a reference point O1 is a center of the polygonal sheet 40.

The polygonal sheet 40 is formed by using a sheet-shaped flexible substrate. A main surface of the polygonal sheet 40 is formed in an approximately octagonal shape. The polygonal sheet 40 is formed in a size that covers the entire surface of the abdomen of the subject 2. The polygonal sheet 40 forms a positioning hole portion 40a having an approximately circular shape.

The positioning hole portion 40a is provided at a position where the center thereof includes the reference point O1 of the polygonal sheet 40. The positioning hole portion 40a functions as a positioning portion that determines a mounting position of the antenna apparatus 4 with respect to the subject 2 when being mounted to the subject 2. For example, when the polygonal sheet 40 is attached to the subject 2 so that an index site (for example, the navel or the like) of a body surface of the subject 2 is positioned at the central portion (reference point O1) in the positioning hole portion 40a, the first receiving antenna 41 to the eighth receiving antenna 48 of the antenna apparatus 4 are mounted correctly at predetermined mounting positions of the body surface of the subject 2. In addition, the main surface of the polygonal sheet 40 does not need to be of an approximately octagonal shape, and, for example, may be of a rectangular shape or the like.

In addition, in the polygonal sheet 40, a cover portion 54 is formed by an elastic member having a thickness that becomes thinner toward the polygonal sheet 40 from a proximal end portion 53, so as to prevent the polygonal sheet 40 from bending at the edge of the cover portion 54 that covers a connection portion 53a between the polygonal sheet 40 and the proximal end portion 53 of the antenna cable 5. The antenna apparatus 4 is placed in the antenna holder and worn by the subject 2 during examination, and by making the shapes of the antenna apparatus 4 and the antenna holder not up-down and/or left-right symmetrical, the antenna apparatus 4 is prevented from being placed in the antenna holder upside-down or inside-out, such that the antenna apparatus 4 is able to be prevented from being worn by the subject 2 in an incorrect orientation. In addition, display to prevent the confusion between top and bottom or front and back of the antenna may be made on the surface of the antenna apparatus 4.

The first receiving antenna 41 and the second receiving antenna 42 are each arranged at positions opposed to each other via the reference point O1 of the polygonal sheet 40. The first receiving antenna 41 and the second receiving antenna 42 are each arranged at positions away from the reference point O1 by equal distances. The first receiving antenna 41 and the second receiving antenna 42 are configured so that an element portion 41a and an element portion 42a are each formed on the polygonal sheet 40 by a printed wiring. The first receiving antenna 41 and the second receiving antenna 42 have an electronic device 41b and an electronic device 42b including an active circuit connected to each of the element portion 41a and the element portion 42a. The electronic device 41b and the electronic device 42b perform impedance matching of each of the first receiving antenna 41 and the second receiving antenna 42, amplification processing including amplification or attenuation of the received a wireless signal, conversion processing for performing the conversion from equilibrium to disequilibrium or the like. The electronic device 41b and the electronic device 42b are mounted by being sealed with the polygonal sheet 40 by a sealing structure 9 which will be described below. The first receiving antenna 41 and the second receiving antenna 42 are connected to the connector unit 49 provided in the polygonal sheet 40 by a planar transmission line (a strip line).

The third receiving antenna 43 and the fourth receiving antenna 44 are arranged at positions that each rotate at 90° in a plane around the reference point O1 with respect to a straight line connecting the centroid of the first receiving antenna 41 and the centroid of the second receiving antenna 42. The third receiving antenna 43 and the fourth receiving antenna 44 are each arranged at positions away from the reference point O1 by equal distances. The third receiving antenna 43 and the fourth receiving antenna 44 are configured so that an element portion 43a and an element portion 44a are each formed on the polygonal sheet 40 by the printed wiring. The third receiving antenna 43 and the fourth receiving antenna 44 have an electronic device 43b and an electronic device 44b including an active circuit connected to each of the element portion 43a and the element portion 44a. The electronic device 43b and the electronic device 44b are mounted by being sealed with the polygonal sheet 40 by the sealing structure 9 which will be described below. The third receiving antenna 43 and the fourth receiving antenna 44 are connected to the connector unit 49 provided in the polygonal sheet 40 by a planar transmission line.

The fifth receiving antenna 45 and the sixth receiving antenna 46 are arranged at positions on the outer peripheral side in the plane than the first receiving antenna 41 and the second receiving antenna 42, and on a straight line extending in a direction 45° with respect to a straight line connecting the first receiving antenna 41 and the second receiving antenna 42, and each centroid thereof is arranged at a position in the plane, respectively. The fifth receiving antenna 45 and the sixth receiving antenna 46 are each arranged at positions on the outer peripheral side in the plane than the first receiving antenna 41 and the second receiving antenna 42. The fifth receiving antenna 45 and the sixth receiving antenna 46 are configured so that an element portion 45a and an element portion 46a are each formed on the polygonal sheet 40 by the printed wiring. The fifth receiving antenna 45 and the sixth receiving antenna 46 have an electronic device 45b and an electronic device 46b including an active circuit connected to each of the element portion 45a and the element portion 46a. The electronic device 45b and the electronic device 46b are mounted by being sealed with the polygonal sheet 40 by the sealing structure 9 which will be described below. The fifth receiving antenna 45 and the sixth receiving antenna 46 are connected to the connector unit 49 provided in the polygonal sheet 40 by a planar transmission line.

The seventh receiving antenna 47 and the eighth receiving antenna 48 are arranged on a straight line extending in a direction 45° with respect to a straight line connecting the centroid of the third receiving antenna 43 and the centroid of the fourth receiving antenna 44, and each centroid thereof is arranged at a position in the plane, respectively. They are arranged at positions rotated by 90° in the plane around the reference point O1 with respect to the fifth receiving antenna 45 and the sixth receiving antenna 46, respectively. The seventh receiving antenna 47 and the eighth receiving antenna 48 are each arranged at the positions on the outer peripheral side in the plane than the first receiving antenna 41 and the second receiving antenna 42. The seventh receiving antenna 47 and the eighth receiving antenna 48 are configured so that an element portion 47a and an element portion 48a are each formed on the polygonal sheet 40 by the printed wiring. The seventh receiving antenna 47 and the eighth receiving antenna 48 have an electronic device 47b and an electronic device 48b each including an active circuit connected respectively to the element portion 47a and the element portion 48a. The electronic device 47b and the electronic device 48b are mounted by being sealed with the polygonal sheet 40 by the sealing structure 9 which will be described below. The seventh receiving antenna 47 and the eighth receiving antenna 48 are connected to the connector unit 49 provided in the polygonal sheet 40, by a planar transmission line.

The antenna cable 5 sends the wireless signals respectively received by the first receiving antenna 41 to the eighth receiving antenna 48 to the antenna connection unit 6, and transmits electric power supplied from the antenna connection unit 6 to the first receiving antenna 41 to the eighth receiving antenna 48, respectively. The antenna cable 5 has the bend stopper portion 51, a flexible portion 52, and the proximal end portion 53. The bend stopper portion 51 is connected to the antenna connection unit 6 by being plugged into the holding portion 614a on the antenna connection unit 6 side. The flexible portion 52 has cores corresponding to the number of the first receiving antenna 41 to the eighth receiving antenna 48. Specifically, the flexible portion 52 has at least eight cores. The proximal end portion 53 is connected to the connector unit 49 at a position away from the straight line passing through the reference point O1 by a predetermined distance.

The antenna apparatus 4 configured in this manner is able to arrange the relative position of each receiving antenna with high accuracy, with respect to the body lumen which is the internal organ of the subject 2 and through which the capsule endoscope 3 passes, by arranging the first receiving antenna 41 to the eighth receiving antenna 48 based on a site becoming an indicator of the body surface of the subject 2. Accordingly, it is possible to easily perform positioning of the antenna apparatus 4 to the subject 2 by the simple action of attaching the antenna apparatus 4 to the subject 2 using the positioning hole portion 40a. In addition, a transparent member, for example, a transparent plastic sheet or the like may be provided in the positioning hole portion 40a.

Figure 10:
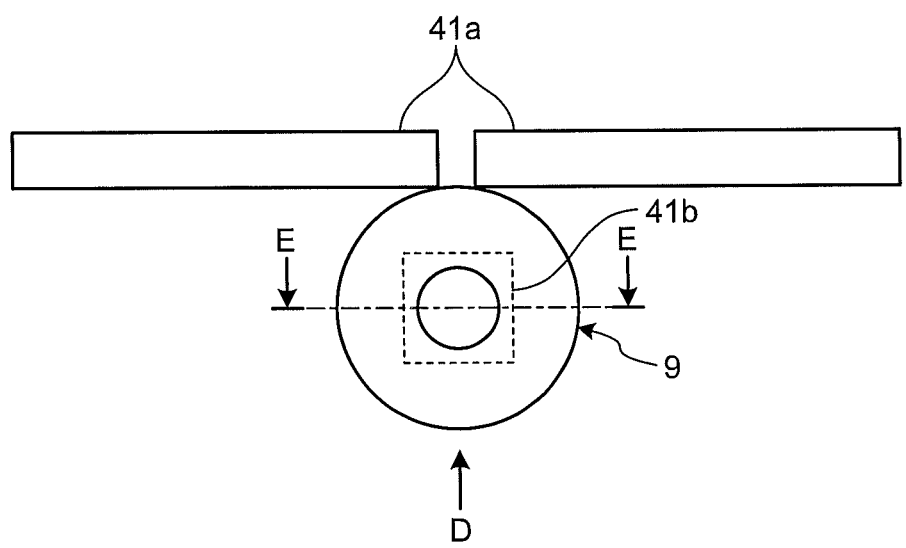
FIG. 10 is a plan view schematically illustrating a configuration of a first receiving antenna and a sealing structure illustrated in FIG. 9.
Figure 11:
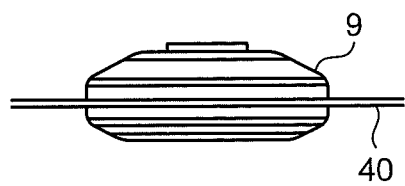
FIG. 11 is a side view seen from a direction of an arrow D illustrated in FIG. 10.
Figure 12:
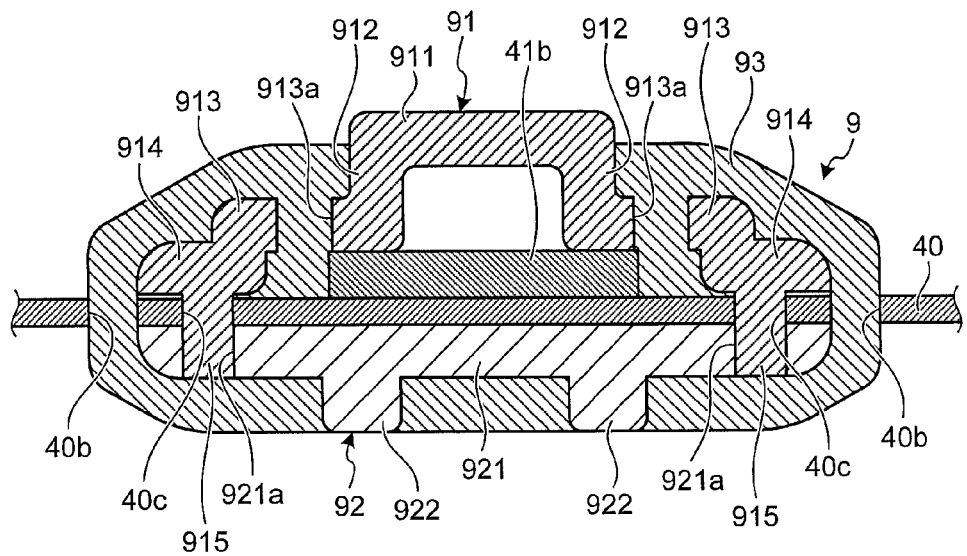
FIG. 12 is a cross-sectional view taken along line E-E illustrated in FIG. 10.
Figure 13:
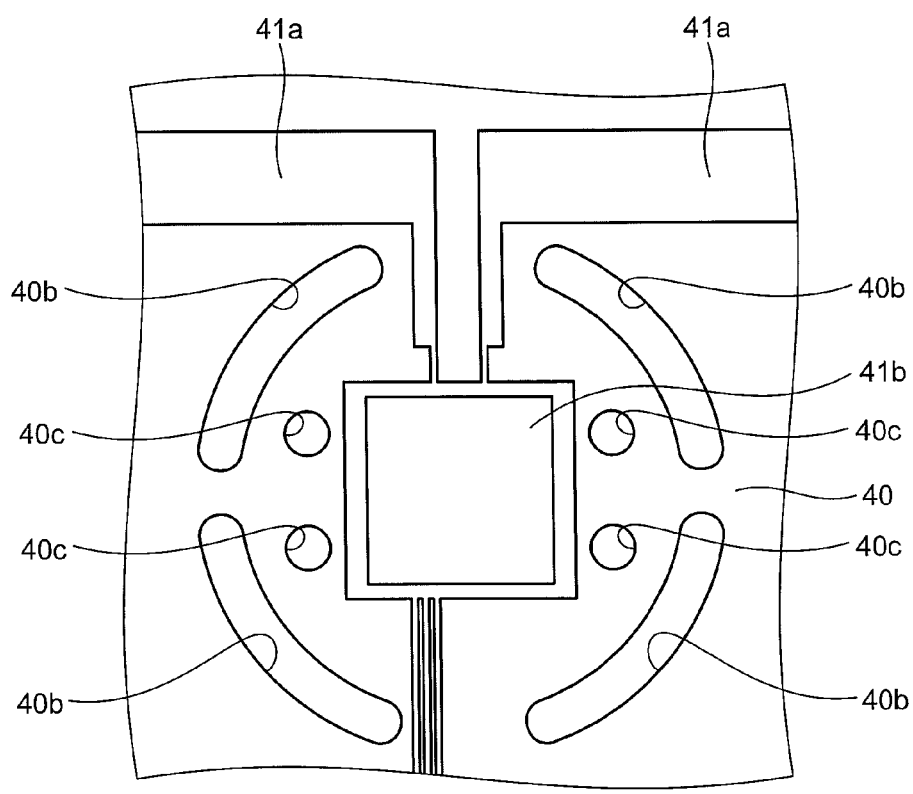
FIG. 13 is a plan view illustrating a main part before an electronic device illustrated in FIG. 9 is sealed by the sealing structure.
Figure 14:
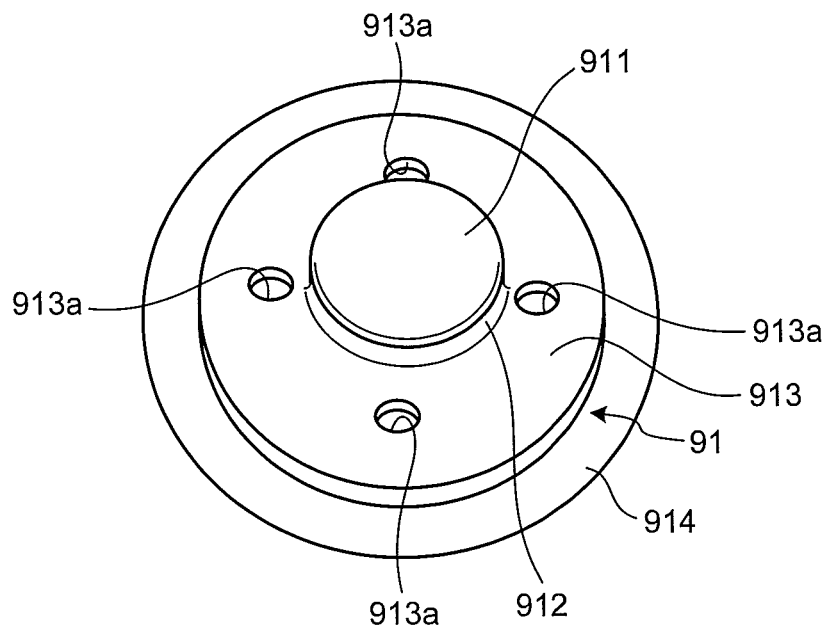
FIG. 14 is an external view illustrating a top side of a first resin plate portion that constitutes the sealing structure according to the first embodiment of the invention.
Figure 15:
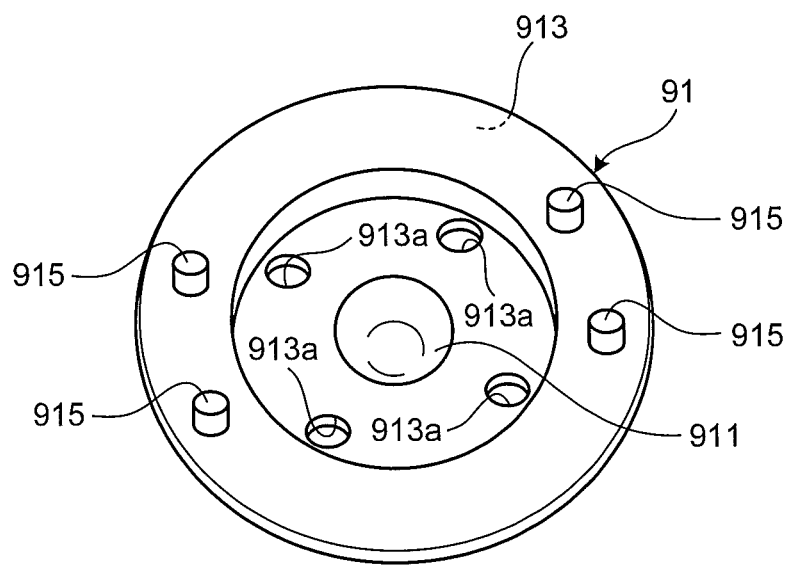
FIG. 15 is an external view illustrating a back side of the first resin plate portion that constitutes the sealing structure according to the first embodiment of the invention.
Figure 16:
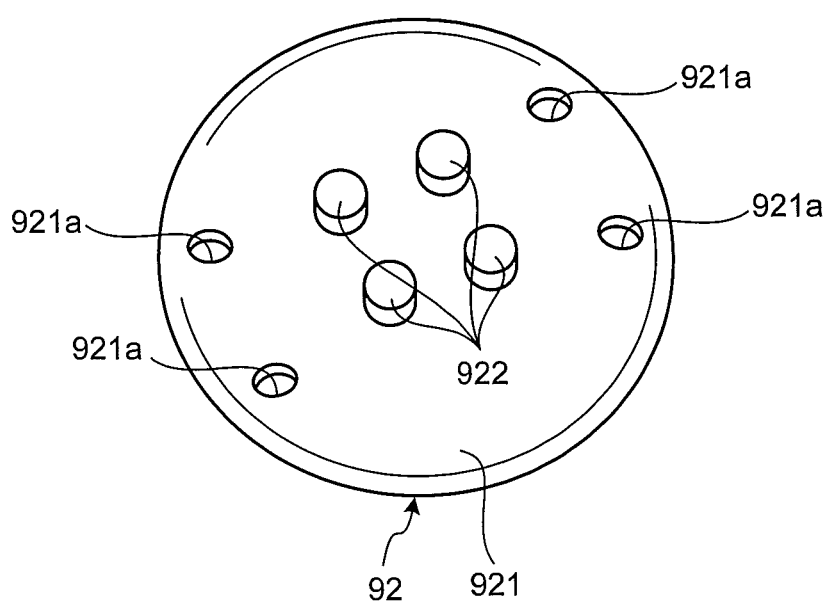
FIG. 16 is an external view illustrating a top side of a second resin plate portion that constitutes the sealing structure according to the first embodiment of the invention.

Here, the configurations of the first receiving antenna 41 and the sealing structure 9 illustrated in FIG. 9 will be described in detail. FIG. 10 is a plan view schematically illustrating a configuration of the first receiving antenna 41 and the sealing structure 9 illustrated in FIG. 9. FIG. 11 is a side view seen from a direction of an arrow D illustrated in FIG. 10. FIG. 12 is a cross-sectional view taken from line E-E illustrated in FIG. 10. FIG. 13 is a plan view illustrating a main part prior to sealing the electronic device 41b illustrated in FIG. 9 by the sealing structure 9. FIG. 14 is an external view illustrating a top side of a first resin plate portion that forms the sealing structure 9. FIG. 15 is an external view illustrating a back side of the first resin plate portion that forms the sealing structure 9. FIG. 16 is an external view illustrating a top side of a second resin plate portion that forms the sealing structure 9.

As illustrated in FIGS. 10 to 16, the first receiving antenna 41 is formed by using a balanced type antenna. Specifically, the first receiving antenna 41 is configured so that two element portions 41a are formed by using a dipole antenna which has a wire on a straight line. The first receiving antenna 41 is configured so that the wires of the two element portions 41a on the straight line are formed in approximately the same length on the straight line in a bilaterally symmetrical manner. Furthermore, the first receiving antenna 41 is configured so that the electronic device 41b is electrically connected to the element portions 41a by a soldering portion that is not illustrated.

The polygonal sheet 40 has a plurality of first sheet communication hole portions 40b that are fan shaped, and a plurality of second sheet communication hole portions 40c having an approximately circular shape formed on the polygonal sheet 40 around the electronic device 41b.

The first sheet communication hole portion 40b has an approximately arc shape having a width, and the plurality of first sheet communication hole portions 40b are formed on the polygonal sheet 40 at every predetermined interval so as to surround the periphery of the electronic device 41b. The first sheet communication hole portions 40b connect the top surface and the back surface of the polygonal sheet 40.

The second sheet communication hole portion 40c has an approximately circular shape, and the plurality of second sheet communication hole portions 40c are formed at every predetermined interval so as to surround the periphery of the electronic device 41b. The second sheet communication hole portions 40c are formed on the inner peripheral side of the first sheet communication hole portions 40b.

The sealing structure 9 includes a first resin plate portion 91 formed on the polygonal sheet 40 around the electronic device 41b and arranged above the electronic device 41b, a second resin plate portion 92 that interposes the electronic device 41b via the polygonal sheet 40, and an elastic body 93 that is provided on the outer periphery of the first resin plate portion 91 and the second resin plate portion 92 and covers a part of the first resin plate portion 91 and the second resin plate portion 92. The outer edge of the sealing structure 9 has an approximately circular shape, and is in contact with the first receiving antenna 41 (does not overlap the element portion 41a).

The first resin plate portion 91 has an approximately circular shape, and is formed by using a harder material than the polygonal sheet 40, for example, a plastic member such as an engineering plastic. The first resin plate portion 91 has a lid portion 911 having an approximately circular shape, an approximately annular-shaped side wall 912 provided extending vertically from the peripheral edge of the lid portion 911, a first plate portion 913 provided extending toward the outer peripheral side from the side wall 912, a second plate portion 914 provided extending toward the outer peripheral side from the first plate portion 913, and a plurality of approximately cylindrical protruding portions 915 that are provided on the back surface of the polygonal sheet 40 from the second plate portion 914, and penetrate through the second sheet communication hole portion 40c of the polygonal sheet 40. Furthermore, the first plate portion 913 is formed with a plurality of hole portions 913a at every predetermined interval. The hole portions 913a provide communication between the electronic device 41b and outside of the first resin plate portion 91. The lid portion 911, the side wall 912, the first plate portion 913, the second plate portion 914, and the protruding portions 915 are integrally formed, by injection molding, so as to continuously extend. In addition, the first resin plate portion 91 is configured so that the side wall 912 abuts against a part of the electronic device 41b and presses the part toward the polygonal sheet 40.

The second resin plate portion 92 has an approximately circular shape, and is formed by using a harder material than the polygonal sheet 40, for example, a plastic member such as an engineering plastic. The second resin plate portion 92 has a bottom portion 921 having an approximately circular shape, and a plurality of protruding portions 922 protruding from the vicinity of the center of the bottom portion 921 at every predetermined interval. The bottom portion 921 is formed with a plurality of fitting portions 921a that are fitted to the protruding portions 915 at the positions opposite to the protruding portions 915 of the first resin plate portion 91. The bottom portion 921 and the protruding portions 922 are integrally formed by injection molding so as to continuously extend.

The elastic body 93 is formed by using a thermoplastic member such as an elastomer. The elastic body 93 is provided on the outer periphery of the first resin plate portion 91 and the second resin plate portion 92 via the plurality of the first sheet communication hole portions 40b, covers a part of the first resin plate portion 91 and the second resin plate portion 92, and is integrally molded so as to press the first resin plate portion 91 and the second resin plate portion 92 against the polygonal sheet 40. Specifically, the elastic body 93 is integrally molded in close contact and fixed with respect to the polygonal sheet 40, the first resin plate portion 91, and the second resin plate portion 92 in a state in which the polygonal sheet 40 and the electronic devices 41b are interposed by the first resin plate portion 91 and the second resin plate portion 92. Furthermore, the elastic body 93 is filled in a gap (an interior) between the first resin plate portion 91 and the electronic device 41b via the hole portion 913a of the first resin plate portion 91. Accordingly, the elastic body 93 is filled in the peripheral edge of the electronic device 41b. Thereupon, the outer edge of the elastic body 93 has an approximately circular shape, and is molded in contact with the element portion 41a.

According to the sealing structure 9 having such a configuration, even if the polygonal sheet 40 is curved by external force, the first resin plate portion 91 and the second resin plate portion 92 alleviate the curvature (bending) of the polygonal sheet 40 in the vicinity of the electronic device 41b. Thus, load is not applied to a soldering portion for connecting the electronic device 41b to the element portion 41a, and it is possible to maintain the reception characteristics of the first receiving antenna 41, and to stably receive the wireless signal. Furthermore, the sealing structure 9 is able to reliably prevent water or the like from entering the electronic device 41b, by the close contact of the elastic body 93 with the polygonal sheet 40. Furthermore, since the sealing structure 9 is formed so that the elastic body 93 comes into contact with the element portion 41a, a difference in the dielectric constant of the elastic body 93 has no influence, and it is possible to maintain the reception characteristics of the first receiving antenna 41. Furthermore, since the simple sealing structure 9 is formed by the first resin plate portion 91, the second resin plate portion 92, and the elastic body 93, it is possible to reduce the cost. In addition, the other electronic devices 42b to 48b are also similarly sealed to the polygonal sheet 40 by the sealing structure 9.

Figure 17:
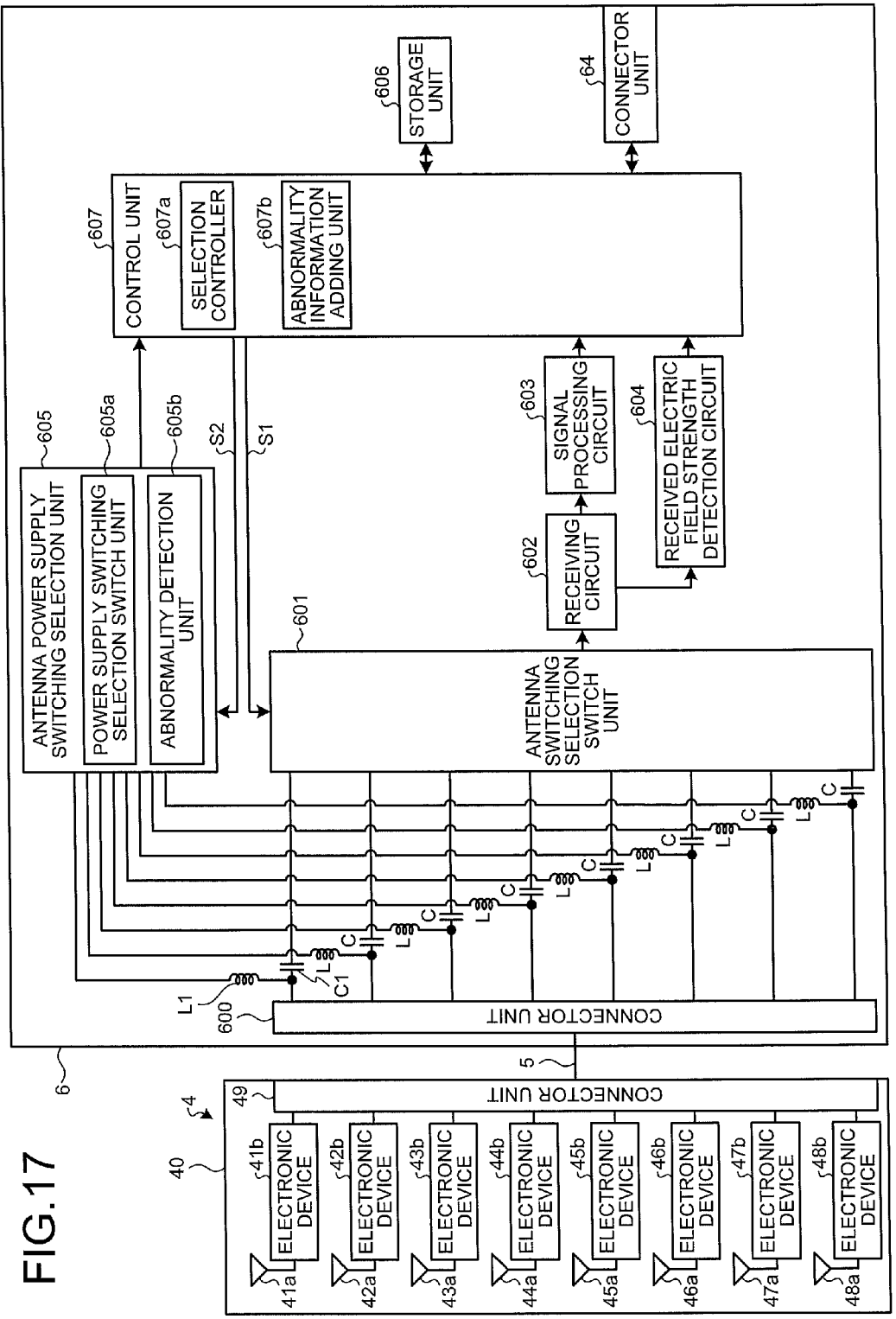
FIG. 17 is a block diagram illustrating a functional configuration of the antenna apparatus and the antenna connection unit according to the first embodiment of the invention.

Next, the function of the antenna connection unit 6 described in FIG. 2 and the antenna apparatus 4 described in FIG. 9 will be described in detail. FIG. 17 is a block diagram illustrating a functional configuration of the antenna apparatus 4 and the antenna connection unit 6. In addition, hereinafter, when referring to any one of the first receiving antenna 41 to the eighth receiving antenna 48, the first receiving antenna 41 (the element portion 41a, and the electronic device 41b) will be simply described.

As illustrated in FIG. 17, the antenna connection unit 6 includes a connector unit 600 to which the antenna cable 5 is connected, an antenna switching selection switch unit 601 that alternatively switches over among the first receiving antenna 41 to the eighth receiving antenna 48, a receiving circuit 602 that performs processing such as demodulation on the wireless signal received via any one of the first receiving antenna 41 to the eighth receiving antenna 48 selected by the antenna switching selection switch unit 601, a signal processing circuit 603 that extracts image data and the like from the wireless signals output from the receiving circuit 602, a received electric field strength detection circuit 604 that detects the received strength based on the strength of the wireless signal output from the receiving circuit 602, an antenna power supply switching selection unit 605 that supplies the electric power to any one of the first receiving antenna 41 to the eighth receiving antenna 48, a storage unit 606 that stores the correction parameters for calibrating the received electric field strength detection circuit 604 and correction parameters for calibrating the first receiving antenna 41 to the eighth receiving antenna 48, the connector unit 64 that performs the transmission and reception with the receiving device 7 in a bi-directional manner, and a control unit 607 that controls the operation of the antenna connection unit 6.

The antenna cable 5 is connected to the connector unit 600 in a freely attachable and detachable manner. The connector unit 600 is electrically connected to the antenna switching selection switch unit 601 and the antenna power supply switching selection unit 605.

The antenna switching selection switch unit 601 is formed by using a mechanical switch, a semiconductor switch, or the like. The antenna switching selection switch unit 601 is electrically connected to each of the first receiving antenna 41 to the eighth receiving antenna 48 via a capacitor C1. In a case where a switching signal S1 for switching the receiving antenna configured to receive the wireless signal is input from the control unit 607, for example, the antenna switching selection switch unit 601 selects the first receiving antenna 41 instructed by the switching signal S1, and outputs the wireless signal received via the selected first receiving antenna 41 to the receiving circuit 602. In addition, the capacitance of the capacitor connected to each of the first receiving antenna 41 to the eighth receiving antenna 48 is equal to the capacitance of the capacitor C1.

The receiving circuit 602 performs predetermined processing such as demodulation and amplification on the wireless signal received via the first receiving antenna 41 selected by the antenna switching selection switch unit 601, and outputs the processed signal to each of the signal processing circuit 603 and the received electric field strength detection circuit 604.

The signal processing circuit 603 extracts the image data from the wireless signal that is input from the receiving circuit 602, performs predetermined processing, for example, various kinds of image processing, A/D conversion processing, or the like on the extracted image data, and outputs the processed image data to the control unit 607. Specifically, the signal processing circuit 603 performs amplification processing, noise reduction processing, or the like on the image data, and outputs the processed image data to the control unit 607.

The received electric field strength detection circuit 604 detects the received strength according to the strength of the wireless signal that is input from the receiving circuit 602, and outputs a received signal strength indicator (RSSI) corresponding to the detected received strength to the control unit 607.

The antenna power supply switching selection unit 605 is electrically connected to each of the first receiving antenna 41 to the eighth receiving antenna 48 via the coil L1. The antenna power supply switching selection unit 605 supplies electric power to the first receiving antenna 41 selected by the antenna switching selection switch unit 601 via the antenna cable 5. The antenna power supply switching selection unit 605 has a power supply switching selection switch unit 605a, and an abnormality detection unit 605b. In addition, the electrical characteristics of the coil connected to each of the first receiving antenna 41 to the eighth receiving antenna 48 are equal to the electrical characteristics of the coil L1.

The power supply switching selection switch unit 605a is formed by using a mechanical switch, a semiconductor switch, or the like. When a selection signal S2 for selecting a receiving antenna configured to supply the electric power from the control unit 607 is input, the power supply switching selection switch unit 605a selects, for example, the first receiving antenna 41 instructed by the selection signal S2, and supplies the electric power only to the selected first receiving antenna 41.

In a case in which an abnormality occurs in the first receiving antenna 41 configured to supply the electric power, the abnormality detection unit 605b outputs to the control unit 607 an abnormality signal indicating that an abnormality has occurred in the first receiving antenna 41 configured to supply the electric power. Specifically, the abnormality detection unit 605b detects a disconnection abnormality or a short circuit abnormality in the first receiving antenna 41 based on the voltage supplied to the first receiving antenna 41 selected by the power supply switching selection switch unit 605a, and outputs the detection result to the control unit 607.

The storage unit 606 is formed by using a semiconductor memory such as a flash memory and a random access memory (RAM) fixedly provided inside the antenna connection unit 6. The storage unit 606 stores image data captured by the capsule endoscope 3, various information corresponding to the image data such as the position information of the capsule endoscope 3, the received strength information and the identification information for identifying the receiving antenna that receives the wireless signal, various programs executed by the antenna connection unit 6, and the like.

The connector unit 64 functions as a communication interface, and performs the transmission and reception with respect to the receiving device 7 in a bi-directional manner.

The control unit 607 is formed by using a CPU or the like. The control unit 607 reads and executes a program from the storage unit 606, and controls the overall operation of the antenna connection unit 6 by performing instructions, the transfer of data, or the like to each unit forming the antenna connection unit 6. In addition, the antenna switching selection switch unit 601, the receiving circuit 602, the signal processing circuit 603, the received electric field strength detection circuit 604, the antenna power supply switching selection unit 605, the storage unit 606, and the control unit 607 function as the processing substrate 63.

The detailed configuration of the control unit 607 will be described. The control unit 607 has a selection controller 607a, and an abnormality information adding unit 607b.

The selection controller 607a selects the receiving antenna that receives the wireless signal transmitted from the capsule endoscope 3, and performs the control of supplying the electric power only to the selected receiving antenna. Specifically, the selection controller 607a selects the receiving antenna for receiving the wireless signal transmitted from the capsule endoscope 3 based on the received strength (the input power) of each of the first receiving antenna 41 to the eighth receiving antenna 48 detected by the received electric field strength detection circuit 604, and performs the control of supplying the electric power only to the selected receiving antenna. For example, the selection controller 607a drives the antenna switching selection switch unit 601 at every predetermined timing, for example, at every 100 msec, sequentially selects the receiving antenna that receives the wireless signal from the first receiving antenna 41 to the eighth receiving antenna 48, and repeatedly performs the processing until the received strength detected by the received electric field strength detection circuit 604 becomes a predetermined value.

When the abnormality detection unit 605b detects an abnormality in any one of the first receiving antenna 41 to the eighth receiving antenna 48, the abnormality information adding unit 607b adds the abnormality information indicating that an abnormality has occurred in any one of the first receiving antenna 41 to the eighth receiving antenna 48, with respect to the wireless signals each received by the first receiving antenna 41 to the eighth receiving antenna 48. Specifically, the abnormality information adding unit 607b adds a flag indicating the abnormality information to the image data in which the signal processing circuit 603 performs the signal processing on the wireless signals each received by the first receiving antenna 41 to the eighth receiving antenna 48.

According to the first embodiment of the invention described above, the electronic devices 41b to 48b mounted on the polygonal sheet 40 are interposed by the first resin plate portion 91 and the second resin plate portion 92 from the top surface and the back surface of the polygonal sheet 40, and the elastic body 91 is integrally molded on the outer periphery of the polygonal sheet 40, the first resin plate portion 91, and the second resin plate portion 92. Accordingly, even if the polygonal sheet 40 is curved by an external force, the first resin plate portion 91 and the second resin plate portion 92 relax the bending of the polygonal sheet 40 in the vicinity of the electronic devices 41b to 48b. As a result, load is not applied to the soldering unit for connecting each of the electronic devices 41b to 48b to the element portions 41a to 48a, it is possible to maintain the reception characteristics of the first receiving antenna 41 to the eighth receiving antenna 48, and it is possible to stably receive the wireless signal.

According to the first embodiment, it is possible to reliably prevent water or the like from entering the electronic devices 41b to 48b, by the close contact (watertightness) of the elastic body 93 with the polygonal sheet 40.

Furthermore, according to the first embodiment, since the elastic body 93 is formed so as to come into contact with the element portions 41a to 48a, a difference in the dielectric constant of the elastic body 93 has no influence, and it is possible to maintain the reception characteristics of the first receiving antenna 41 to the eighth receiving antenna 48.

In addition, according to the first embodiment, since the sealing structure 9 is formed by the first resin plate portion 91, the second resin plate portion 92, and the elastic body 93, it is possible to reduce the cost.

In addition, in the first embodiment, the sealing structure 9 has an approximately circular shape, but may have an oval shape or a rectangular shape.

First Modified Example of First Embodiment

Figure 18:
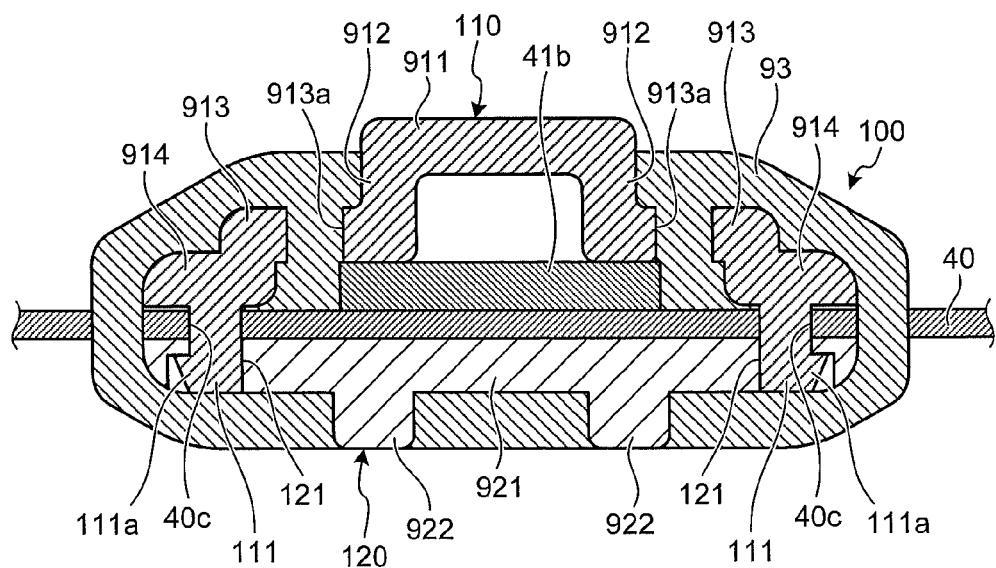
FIG. 18 is a cross-sectional view illustrating a configuration of a sealing structure according to a first modified example of the first embodiment of the invention.

In addition, in the first embodiment of the invention, it is possible to change the shape of the protruding portions formed on the first resin plate portion and the fitting portions formed on the second resin plate portion. FIG. 18 is a cross-sectional view illustrating a configuration of a sealing structure according to a first modified example of the first embodiment. In addition, the same structures as the first embodiment described above will be described being denoted by the same reference numerals.

As illustrated in FIG. 18, a sealing structure 100 includes a first resin plate portion 110, a second resin plate portion 120, and an elastic body 93.

The first resin plate portion 110 includes a lid portion 911, a side wall 912, a first plate portion 913, a second plate portion 914, and a protruding portion 111. A plurality of protruding portions 111 are provided in the vertical direction from the second plate portion 914. The protruding portion 111 has a claw portion 111a which functions as an engagement portion that is engaged with the fitting portion 121. The lid portion 911, the side wall 912, the first plate portion 913, the second plate portion 914, and the protruding portions 111 are integrally formed by injection molding so as to continuously extend, using a plastic member. Furthermore, the first resin plate portion 110 is configured so that the side wall 912 and the first plate portion 913 press the electronic device 41b toward the polygonal sheet 40.

The second resin plate portion 120 includes a bottom portion 921, protruding portions 922, and fitting portions 121. A plurality of fitting portions 121 are formed at positions opposite to the protruding portions 111 of the first resin plate portion 110. The fitting portions 121 are formed in an approximately L shape in a cross section. The bottom portion 921, the protruding portions 922, and the fitting portions 121 are integrally formed by injection molding so as to continuously extend, using a plastic member.

According to the first modified example of the first embodiment of the invention described above, since the protruding portions 111 are formed with the claw portions 111a toward the outer peripheral side, it is possible to reliably prevent the first resin plate portion 110 and the second resin plate portion 120 from being disengaged due to external force.

Furthermore, according to the first modified example of the first embodiment, because elastomer is formed after the first resin plate portion 110 and the second resin plate portion 120 are attached at a plurality of positions by fitting to one another, upon setting into a mold, the first resin plate portion 110 and the second resin plate portion 120 are preventable from being dislocated, and re-attachment is infallibly preventable.

Additionally, according to the first modified example of the first embodiment, it is possible to omit an additional step (a bonding step), such as fixing the first resin plate portion 110 and the second resin plate portion 120 using an adhesive so as not to be disengaged after bonding, and it is possible to reduce the processing cost.

In addition, according to the first modified example of the first embodiment, although the claw portion 111a is provided as the engagement portion, for example, the protruding portion 111 may be provided with a helical groove. Furthermore, the protruding portions 111 may be engaged with the fitting portions 121, by providing irregularities on the surface of each of the protruding portions 111 and the fitting portions 121 to increase a surface area coming into contact with each other.

Second Modified Example of First Embodiment

Figure 19:
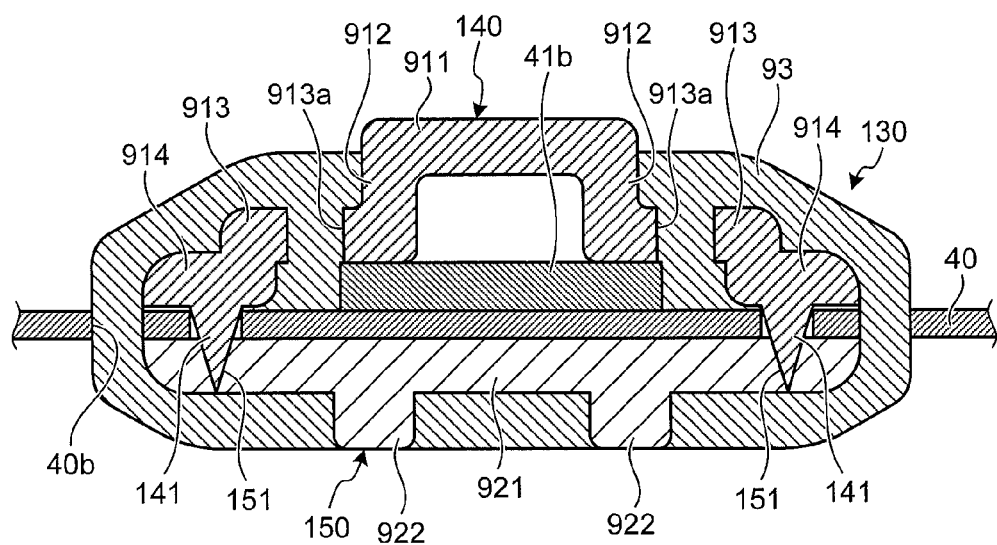
FIG. 19 is a cross-sectional view illustrating a configuration of a sealing structure according to a second modified example of the first embodiment of the invention.

FIG. 19 is a cross-sectional view illustrating a configuration of a sealing structure according to a second modified example of the first embodiment of the invention. In addition, the same configurations as the first embodiment described above will be described while being denoted by the same reference numerals.

As illustrated in FIG. 19, a sealing structure 130 includes a first resin plate portion 140, a second resin plate portion 150, and an elastic body 93.

The first resin plate portion 140 includes a lid portion 911, a side wall 912, a first plate portion 913, a second plate portion 914, and protruding portions 141. A plurality of protruding portions 141 are provided in the vertical direction from the second plate portion 914. The protruding portions 141 are formed in a conical shape so as to become sharper toward the distal end thereof. The lid portion 911, the side wall 912, the first plate portion 913, the second plate portion 914, and the protruding portions 141 are integrally formed by injection molding so as to continuously extend, using a plastic member.

The second resin plate portion 150 includes a bottom portion 921, a protruding portion 922, and a fitting portion 151. A plurality of fitting portions 151 are formed at positions opposite to the protruding portions 141 of the first resin plate portion 140. The fitting portions 151 are formed cylindrically shaped such that a diameter thereof becomes smaller toward an end thereof. The bottom portion 921, the protruding portions 922, and the fitting portions 151 are integrally formed by injection molding so as to continuously extend, using a plastic member. In addition, the fitting portions 151 may be notches or the like.

In the sealing structure 130 configured as described above, when the first resin plate portion 140 and the second resin plate portion 150 are connected to each other, the protruding portions 141 press and deform the fitting portions 151. Accordingly, it is possible to prevent the first resin plate portion 140 and the second resin plate portion 150 from being disengaged by external force.

According to the second modified example of the first embodiment of the invention described above, it is possible to reliably prevent the first resin plate portion 140 and the second resin plate portion 150 from being disengaged by external force.

Second Embodiment

Next, a second embodiment of the invention will be described. The second embodiment is different from the first embodiment described above in a shape of the first resin plate portion. For this reason, the first resin plate portion will be described below. In addition, the same structures as the first embodiment described above will be described being denoted by the same reference numerals.

Figure 20:
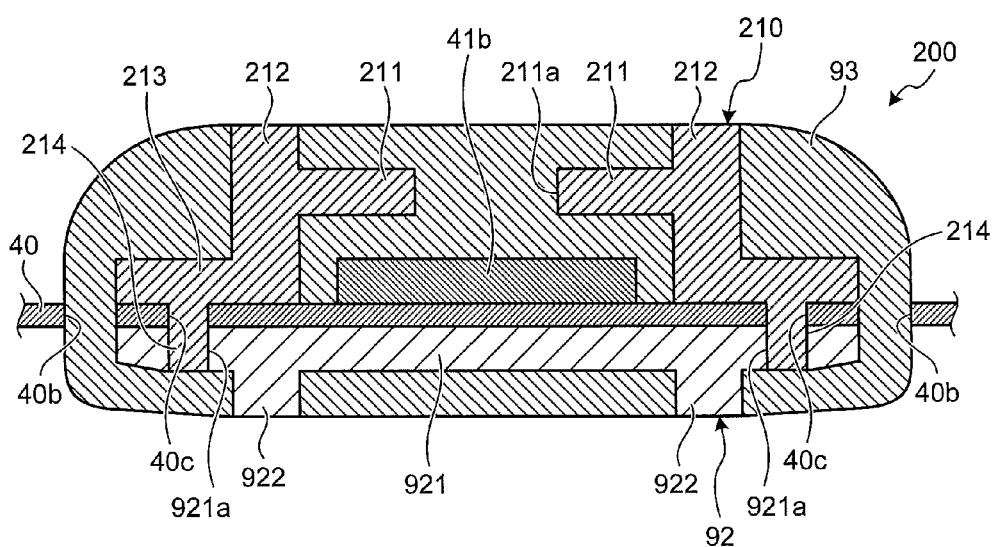
FIG. 20 is a cross-sectional view illustrating a configuration of a sealing structure according to a second embodiment of the invention.

FIG. 20 is a cross-sectional view illustrating a configuration of a sealing structure according to the second embodiment. A sealing structure 200 illustrated in FIG. 20 includes a first resin plate portion 210, a second resin plate portion 92, and an elastic body 93.

The first resin plate portion 210 includes a lid portion 211 having an approximately circular shape, a side wall 212 which is formed along the peripheral edge of the lid portion 211 and has an annular shape, a plate portion 213 which is formed on the outer peripheral side from the side wall 212, and protruding portions 214 which are formed in the vertical direction at a predetermined interval from the plate portion 213. The lid portion 211 is formed with an aperture portion 211a having an approximately circular shape. The lid portion 211, the side wall 212, the plate portion 213, and the protruding portions 214 are formed integrally by injection molding so as to continuously extend, using a plastic member.

According to the sealing structure 200 configured in this manner, the first resin plate portion 210 does not directly contact the top surface of the electronic device 41b, and even if the first resin plate portion 210 is pressed by the mold upon a molding process for the elastic body 93, by performing molding in a state in which the pressing force is not directly applied to the electronic device 41b, it is possible to form the sealing structure 200 without applying unnecessary load to the electronic device 41b. Since the elastic body 93 is filled in the gap between the first resin plate portion 210 and the electronic device 41b via the aperture portion 211a, the electronic device 41b is able to be fixed after molding.

According to the second embodiment of the invention described above, it is possible to prevent the unnecessarily large load from being applied to the electronic device 41b at the time of the molding process of the sealing structure 200.

First Modified Example of Second Embodiment

Figure 21:
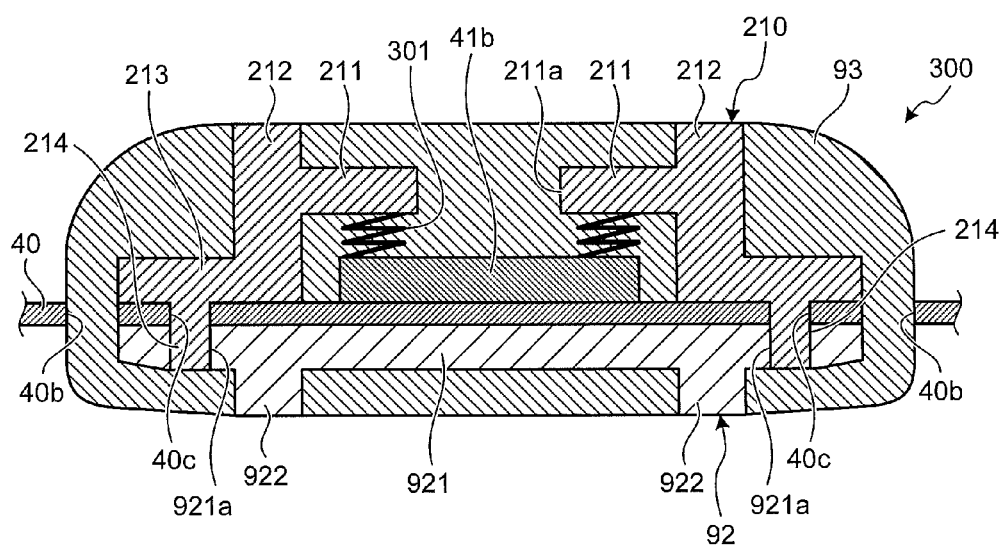
FIG. 21 is a cross-sectional view illustrating a configuration of a sealing structure according to a first modified example of the second embodiment of the invention.

In addition, in the second embodiment, it is also possible to change the shape of the first resin plate. FIG. 21 is a cross-sectional view illustrating a configuration of a sealing structure according to a first modified example of the second embodiment. In addition, the same structures as the second embodiment described above will be described being denoted by the same reference numerals.

A sealing structure 300 illustrated in FIG. 21 has a first resin plate portion 210, and an elastic member 301 that is provided between the first resin plate portion 210 and the electronic device 41b and is biased in a direction in which the first resin plate portion 210 and the electronic device 41b separate from each other. The elastic member 301 is formed by using a spring, a rubber, or the like.

According to the sealing structure 300 configured as described above, it is possible to mold the elastic body 93, while reliably fixing the electronic device 41*b*, without applying unnecessary pressure to the electronic device 41*b* during processing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A sealing structure that seals an electronic device mounted on a substrate that is bendable, the sealing structure comprising:
    a plate portion that is formed with a harder material than the substrate and interposes the electronic device via the substrate from a top surface and a back surface of the substrate on which the electronic device is mounted; and
    an elastic body that is provided on an outer periphery of the plate portion to cover a part of the plate portion and integrally molded so as to press the plate portion against the substrate.

2. The sealing structure according to claim 1,
    wherein the elastic body is molded via a communication hole portion that is provided on the substrate and through which the top surface and the back surface are in communication with each other.

3. The sealing structure according to claim 1,
    wherein the plate portion has a hole portion through which the electronic device and outside of the plate portion are in communication with each other, and
    the elastic body is filled, via the hole portion, in a gap between the plate portion and the electronic device.

4. The sealing structure according to claim 1,
    wherein the plate portion has an aperture portion through which the top surface of the electronic device is exposed to outside of the plate portion, and
    the elastic body is filled, via the aperture portion, in a gap between the plate portion and the electronic device.

5. The sealing structure according to claim 1, further comprising:
    an elastic member that is provided between the plate portion and the electronic device and imparts a bias in a direction in which the plate portion and the electronic device separate from each other.

6. The sealing structure according to claim 1,
    wherein the substrate has an antenna unit that receives a wireless signal, and
    an outer edge of the elastic body is approximately circular shaped and in contact with the antenna unit.

7. The sealing structure according to claim 1,
    wherein the plate portion has
        a first plate portion that is positioned on the top surface side, and
        a second plate portion that is positioned on the back surface side and interposes, with the first plate portion via the substrate, the electronic device,
    the first plate portion is formed with a protruding portion that protrudes toward the back surface through the substrate, and
    the second plate portion is formed with a fitting portion that is at a position opposite to the protruding portion and is fitted to the protruding portion.

8. The sealing structure according to claim 7,
    wherein the protruding portion further has an engagement portion engaged with the fitting portion.

9. An antenna apparatus that receives a wireless signal transmitted from a capsule endoscope introduced into a subject, the antenna apparatus comprising:
    a substrate that is bendable;
    an antenna unit that is mounted on the substrate and receives the wireless signal;
    an electronic device that is mounted on the substrate and connected to the antenna unit to perform a predetermined process on the wireless signal received by the antenna unit; and
    a sealing structure that seals the electronic device, wherein the sealing structure has:
        a plate portion that is formed with a harder material than the substrate and interposes the electronic device via the substrate from a top surface and a back surface of the substrate on which the electronic device is mounted; and
        an elastic body that is provided on an outer periphery of the plate portion to cover a part of the plate portion and integrally molded so as to press the plate portion against the substrate.

* * * * *